(12) United States Patent
Stephens et al.

(10) Patent No.: US 7,294,135 B2
(45) Date of Patent: Nov. 13, 2007

(54) CONTROL HANDLE FOR INTRALUMINAL DEVICES

(75) Inventors: Adam Stephens, Norwalk, CT (US); Kazuna Tanaka, Cos Cob, CT (US); Jeffrey Kapec, Westport, CT (US); Peter George Strickler, Tewksbury, MA (US); Nasser Rafiee, Andover, MA (US); Steven Dapolito, Brookline, NH (US); Michael S. Noone, Londonderry, NH (US)

(73) Assignee: Medtronic Vascular, Inc, Santa Rosa, CA (US)

( * ) Notice: Subject to any disclaimer, the term of this patent is extended or adjusted under 35 U.S.C. 154(b) by 854 days.

(21) Appl. No.: 10/392,517

(22) Filed: Mar. 20, 2003

(65) Prior Publication Data

US 2004/0186511 A1    Sep. 23, 2004

(51) Int. Cl.
*A61F 2/84* (2006.01)
*A61F 2/01* (2006.01)

(52) U.S. Cl. .................... 606/108; 606/200
(58) Field of Classification Search ............ None
See application file for complete search history.

(56) References Cited

U.S. PATENT DOCUMENTS

| | | | |
|---|---|---|---|
| 3,774,605 A | 11/1973 | Jewett | |
| 3,996,938 A | 12/1976 | Clark, III | |
| 4,401,433 A | 8/1983 | Luther | |
| 4,616,648 A | 10/1986 | Simpson | |
| 5,133,364 A | 7/1992 | Palermo et al. | |
| 5,295,492 A | 3/1994 | Sellers | |
| 5,346,498 A | 9/1994 | Greelis et al. | |
| 5,591,196 A | 1/1997 | Marin | 606/198 |
| 5,605,162 A | 2/1997 | Mirzaee et al. | |
| 5,779,722 A * | 7/1998 | Shturman et al. | 606/159 |
| 5,968,052 A | 10/1999 | Sullivan, III et al. | |
| 6,325,777 B1 | 12/2001 | Zadno-Azizi et al. | |
| 6,358,199 B1 * | 3/2002 | Pauker et al. | 604/172 |
| 6,398,755 B1 * | 6/2002 | Belef et al. | 606/108 |
| 6,500,166 B1 | 12/2002 | Zadno Azizi et al. | |
| 6,709,667 B1 * | 3/2004 | Lowe et al. | 606/135 |
| 7,083,618 B2 * | 8/2006 | Couture et al. | 606/51 |
| 2002/0095204 A1 | 7/2002 | Thompson et al. | |
| 2002/0161389 A1 | 10/2002 | Boyle et al. | |

FOREIGN PATENT DOCUMENTS

| | | |
|---|---|---|
| DE | 4417637 A1 | 11/1995 |
| DE | 19815119 C1 | 1/2000 |
| EP | 0873733 | 10/1998 |
| EP | 0943302 | 9/1999 |

* cited by examiner

*Primary Examiner*—Glenn K. Dawson
(74) *Attorney, Agent, or Firm*—James F. Crittenden

(57) ABSTRACT

A control handle for an intraluminal device includes a handle housing having a first end and a second end, the handle housing having a lumen. A roller assembly is disposed at a first end of the lumen. The roller assembly comprises a first roller and a base. The lumen is interposed between the first roller and the base. A clamp assembly is disposed at the second end of the lumen. The clamp assembly comprises a first clamp element and a second clamp element. The lumen is interposed between the first clamp element and the second clamp element. A closure mechanism is configured to effect movement between the first clamp element and the second clamp element and between the first roller and the base. The control handle further includes a turn device operably connected to the roller assembly.

49 Claims, 5 Drawing Sheets

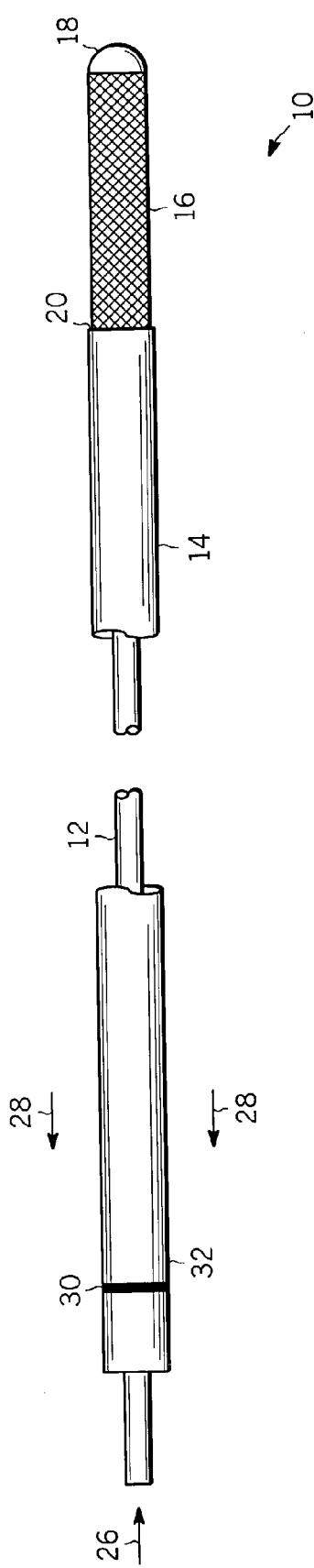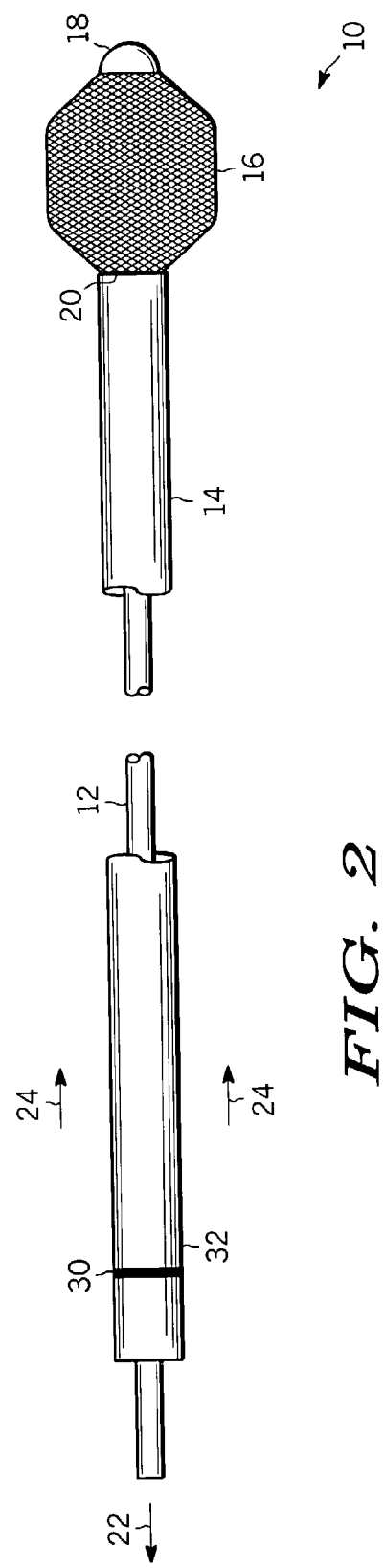
FIG. 1 —PRIOR ART—
FIG. 2 —PRIOR ART—

CONTROL HANDLE FOR INTRALUMINAL DEVICES

TECHNICAL FIELD

This invention relates generally to intraluminal devices, and more particularly, to a control handle for activating or deploying an intraluminal device at a target site.

BACKGROUND OF THE INVENTION

Stenotic lesions may comprise a hard, calcified substance and/or a softer thrombus material, each of which forms on the lumen walls of a blood vessel and restricts blood flow therethrough. Intraluminal treatments such as balloon angioplasty, stent deployment, atherectomy, and thrombectomy are well known and have been proven effective in the treatment of such stenotic lesions. These treatments often involve the insertion of a therapy catheter into a patient's vasculature.

One class of vascular catheters used to treat stenotic lesions is distal protection devices (DPD's). DPD's include, but are not limited to, filter devices and occluder devices. Filter devices are positioned distally from a stenoic lesion to capture stenotic debris that may be released during an intraluminal treatment, such as a balloon angioplasty or a thrombectomy. An occluder device is positioned distally from a stenotic lesion and may be used to block stenotic debris released during an intraluminal treatment, to catch a blood clot when pulled from a blood vessel, and the like.

One type of DPD utilizes a "push-pull" mechanism to deploy the apparatus at the distal end of the DPD. This type of DPD comprises an inner member such as a core wire or guidewire housed within an outer hollow sheath or hypo tube. Either the core wire or the hypo tube is attached to, for example, a filter of the filter device or an occluder of the occluder device. During an intraluminal treatment, the DPD is inserted into a patient's blood vessel until the filter or occluder is located distal to the lesion. By coaxially pushing or pulling the core wire and/or hypo tube relative to each other, the filter or occluder is expanded to an operational diameter. Once treatment is completed, the core wire and/or hypo tube are again coaxially pulled or pushed relative to each other and the filter or occluder is contracted to a removable diameter and the DPD is removed from the patient.

Deployment of DPD's that utilize push/pull mechanisms without damage to the DPD's is difficult. Certain DPD devices utilize fine core wire, such as those having a diameter of 0.013 inches or less, and fine hypo tubes, such as those having a diameter of 0.014 inches or less, both of which may be easily crimped or kinked. In addition, such DPD's may require 1.0 or more pound force to move the hypo tube relative to the core wire, especially when the DPD is disposed through tortuous vasculature. Further, surgical-grade coatings may be applied to such devices for a variety of purposes, such as to reduce trauma to surrounding tissue and/or to reduce risk of infection. If precautions are not taken, the coating may be scraped off the devices during deployment.

Other intraluminal devices also utilize coaxial push and/or pull mechanisms for deployment. For example, one class of self-expanding tubular stents is mounted on an inner catheter and is held in a collapsed configuration by a slidable sheath. Typically, the stent is released in a blood vessel by sliding the sheath proximally off the stent while holding the inner catheter in a fixed longitudinal position in the patient. Current methods of deploying the stent, however, such as sliding thumb buttons and telescoping hypodermic tubes, may cause unintentional advancement of the inner catheter through the sheath and, hence, unintentional misplacement of the stent.

Accordingly, it is desirable to provide a control handle that is configured to accurately deploy an intraluminal device that utilizes a push and/or pull mechanism for deployment. It is also desirable to provide a control handle that does not buckle or kink the inner member and does not scrape off any surgical-grade coating applied to the outer sheath and/or the inner member. Further, it is desirable to provide a control handle that may be removed completely from the intraluminal device during a medical procedure so that the device may be inserted into or removed from a patient or so that one or more other intraluminal procedures may be performed. Other desirable features and characteristics of the present invention will become apparent from the subsequent description and the appended claims, taken in conjunction with the accompanying drawings.

SUMMARY OF THE INVENTION

According to an exemplary embodiment of the invention, there is provided a control handle for an intraluminal device. The control handle comprises a handle housing having a lumen, the handle housing having a first end and a second end. A roller assembly is disposed at a first end of the lumen. The roller assembly comprises a first roller and a base, with the lumen interposed between the first roller and the base. A clamp assembly is disposed at a second end of the lumen. The clamp assembly comprises a first clamp element and a second clamp element, with the lumen interposed between the first clamp element and the second clamp element. A closure mechanism is configured to effect movement between the first clamp element and second clamp element and between the first roller and the base. The control handle further comprises a turn device that is operably connected to the roller assembly.

According to another exemplary embodiment of the invention, there is provided a control handle for effecting movement of an outer hollow tube relative to an inner member coaxially movably disposed within the outer hollow tube and extending beyond the outer hollow tube at a first end of the outer hollow tube. The control handle comprises a handle housing having a first axis, a first end and a second end. A roller assembly is disposed at least partially within the handle housing and comprises a first roller and a base. The first roller and the base are aligned substantially symmetric about an axis parallel to the first axis and are disposed a sufficient distance from each other so that the outer hollow tube may be interposed between the first roller and the base. A clamp mechanism is disposed within the handle housing and comprises a first clamp element and a second clamp element. The first and second clamp elements are aligned substantially symmetric about an axis parallel to the first axis and are disposed a sufficient distance from each other so that the inner member may be interposed between the first and second clamp elements. The control handle further comprises a closure mechanism configured to effect movement between the first and second clamp elements so that the inner member may be secured between the first and second clamp elements to prevent movement of the inner member relative to the control handle along the first axis and to effect movement between the first roller and the base so that the first roller may make sufficient contact with the outer hollow tube. A turn device is operably connected to the roller assembly and configured to effect rotational movement of the first roller upon rotation of the turn device.

According to a further exemplary embodiment of the invention, there is provided a control handle for moving an outer hollow member of an intraluminal device having an inner member coaxially movably disposed within the outer hollow member and extending from an end of the outer hollow member. The control handle comprises a handle housing having a first axis, a first end and a second end. A clamp mechanism is disposed within the handle housing and is configured to secure the inner member against movement parallel to the first axis. A roller assembly is disposed within the handle housing and comprises a first roller and a second roller. The first roller and second roller are configured so that the outer hollow member may be interposed therebetween. A closure mechanism is configured to effect movement between the first roller and the second roller so that, when interposed between the first and second rollers, the outer hollow member may make sufficient contact with the first roller. A turn device is connected to the first roller so that, upon rotation of the turn device, the first roller moves the outer hollow member coaxially relative to the inner member.

According to yet another exemplary embodiment of the invention, there is provided a control handle for actuating an intraluminal device that uses a push and/or pull mechanism, the intraluminal device comprising an inner member movably disposed within an outer hollow member. The control handle comprises a handle housing having a first axis, a clamp assembly disposed within the handle housing and configured to prevent movement of the inner member along the first axis and a roller assembly disposed within the handle housing and configured to move the outer hollow member along the first axis. The control handle further comprises a turn device connected to the roller assembly and configured to actuate the roller assembly.

According to yet a further exemplary embodiment of the invention, there is provided a control handle for an intraluminal device. The control handle comprises a handle housing comprising a lumen, the handle housing having a first end and a second end. A roller assembly is disposed at a first end of the lumen and comprises a first roller and a base. The lumen is interposed between the first roller and the base. A clamp assembly is disposed at a second end of the lumen and comprises a first clamp element and a second clamp element. The lumen is interposed between the first clamp element and the second clamp element. A closure mechanism is operably connected to the first roller assembly and the clamp assembly. A turn device is operably connected to the roller assembly.

BRIEF DESCRIPTION OF THE DRAWINGS

The following drawings are illustrative of particular embodiments of the invention and therefore do not limit the scope of the invention, but are presented to assist in providing a proper understanding. The drawings are not to scale and are intended for use in conjunction with the explanations in the following detailed description. The present invention will hereinafter be described in conjunction with the appended drawings, wherein like numerals denote like elements, and;

FIG. 1 is an illustration of a distal protection device, shown with a filter device in a collapsed configuration;

FIG. 2 is an illustration of a distal protection device, shown with a filter device in a deployed configuration;

DETAILED DESCRIPTION OF EXEMPLARY EMBODIMENTS

Figure 3:
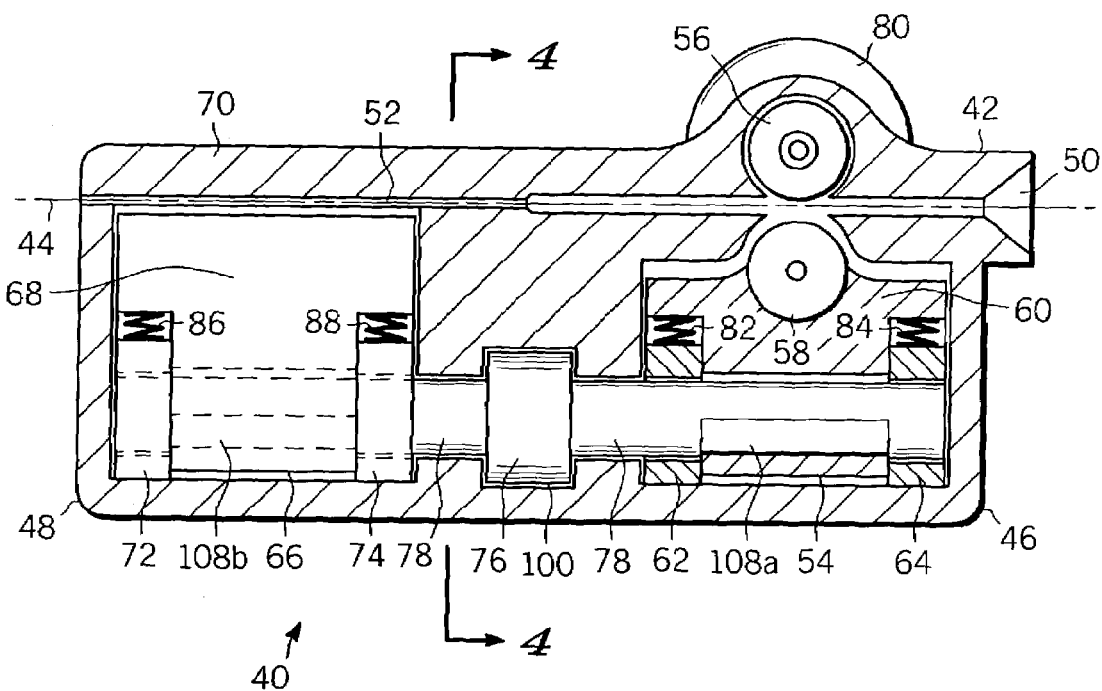
FIG. 3 is a cross-sectional view of a control handle for in intraluminal device in accordance with an exemplary embodiment of the invention, the control handle being in an open position.

The following description is exemplary in nature and is not intended to limit the scope, applicability, or configuration of the invention in any way. Rather the following description provides a convenient illustration for implementing exemplary embodiments of the invention. Various changes to the described embodiments may be made in the function and arrangements of the elements described herein without departing from the scope of the invention.

The various embodiments of the present invention include a control handle for any suitable intraluminal device that utilizes a push and/or pull mechanism for deployment or collapsing of a collapsed expandable apparatus, such as an expandable filter, occluder, stent, balloon, etc., which is located at a first (distal) end of the device. In one class of such intraluminal devices, such as filters, occluders and funnel-shaped devices, when an outer member of the device, such as a sheath or outer hollow tube, is pushed away from the clinician, the apparatus is expanded for deployment in operation mode; in certain of these devices, when the sheath or tube is pulled toward the clinician, the apparatus is collapsed, such as for removal. In another class of such intraluminal devices, such as self-expanding stents, when the sheath or tube is pulled toward the clinician, the apparatus is allowed to expand for deployment in an operation mode.

One example of intraluminal devices that operate by such push-pull mechanisms and that may be used with the control handle of the present invention includes distal protection devices ("DPDs"). An example of a DPD is an expandable filter device 10, such as that illustrated FIGS. 1 and 2. It will be appreciated that while expandable filter device 10 is illustrated in FIGS. 1 and 2 as an example of a DPD, it will be appreciated that other types of DPDs, including occluders, may also be utilized. Expandable filter device 10 includes an inner member 12, such as a core wire or a guidewire, and an outer hollow member 14, such as a sheath or a hypo tube, movably disposed thereabout. Core wire 12 extends beyond hypo tube 14 at a proximal end 32 of hypo tube 14. A filter apparatus 16 surrounds core wire 12 and has a distal end fixed to a core wire distal end 18 and a proximal end fixed to a hypo tube distal end 20. To expand filter apparatus 16, core wire 12 is pulled and hypo tube 14 is pushed, as shown by arrows 22 and 24, respectively, in FIG. 2. The relative displacement of core wire 12 and hypo tube 14 moves the ends of filter apparatus 16 toward each other, forcing the middle region of filter apparatus 16 to expand. To collapse filter apparatus 16, core wire 12 is pushed and hypo tube 14 is pulled as shown by the arrows 26 and 28, respectively, in FIG. 1. This reverse manipulation draws the ends of filter apparatus apart, pulling the middle region of filter apparatus radially inward toward core wire 12.

The dimensions of these types of intraluminal devices can be quite small. For example, for some devices, the diameter of the core wire may be as small as 0.013 inches or even smaller. Similarly, the diameter of the hypo tube may be 0.014 inches or even smaller. Because of such small dimensions, it is often difficult for a clinician to see the proximal end of the hypo tube. Thus, as illustrated in FIGS. 1 and 2, such intraluminal devices may comprise a marker 30 that is positioned at proximal end 32 of the hypo tube, that is, the end opposite the filter apparatus end, and which can be more readily viewable by a clinician.

Figure 4:
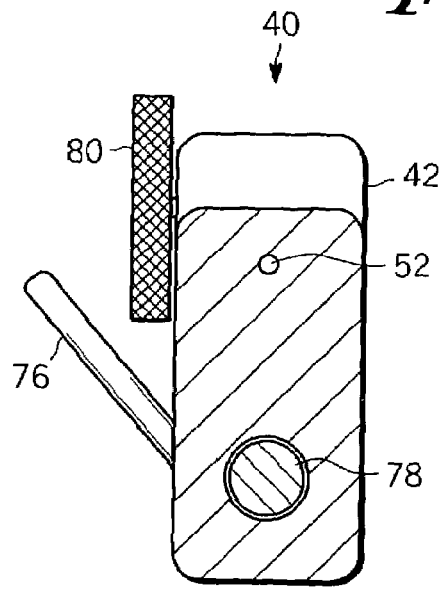
FIG. 4 is a cross-sectional view of the control handle of FIG. 3, taken across the axis 4-4.
Figure 5:
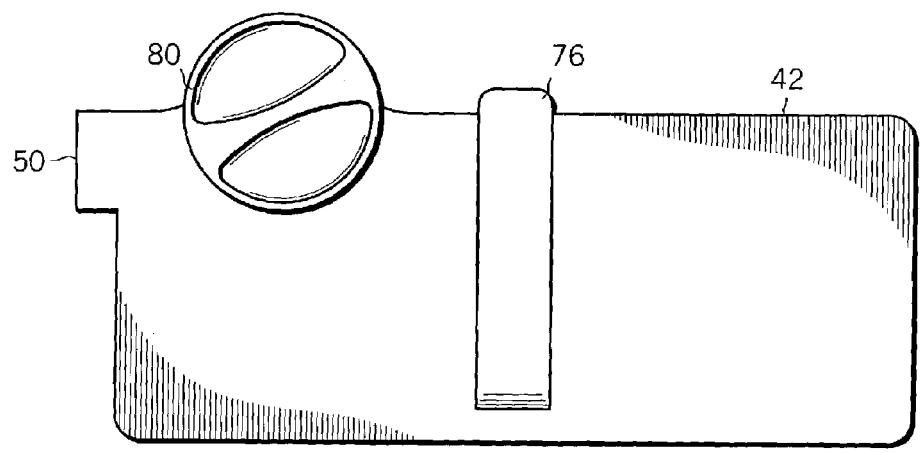
FIG. 5 is a front view of the control handle of FIG. 3 in a closed position.

Referring now to FIGS. 3-5, in one exemplary embodiment of the present invention, a control handle 40 for an intraluminal device is illustrated. Control handle 40 comprises a housing 42 having a first, preferably longitudinal, axis 44, a first end 46 and a second end 48. At first end 46 of housing 42, control handle 40 comprises an entry port 50 configured to receive an inner member, such as a core wire, and an outer member, such as a hypo tube, of an intraluminal device. Entry port 50 is connected to a lumen 52, which is parallel to longitudinal axis 44 and which extends from entry port 50 to approximately second end 48 of housing 42, although it will be appreciated that lumen 52 may terminate at any point beyond a clamp assembly 66, which is introduced in more detail below.

Housing 42 may be formed from any suitable engineering-grade polymers or metals. Examples of suitable polymers include polycarbonates, nylon, styrene copolymers and the like. Suitable metals may include stainless steel, aluminum and the like.

Control handle 40 further comprises a roller assembly 54 positioned proximate to first end 46 of housing 42. Roller assembly 54 comprises a first roller or drive roller 56 and a base 58. First roller 56 and base 58 are aligned substantially symmetric about an axis parallel to longitudinal axis 44. Base 58 may comprise any suitable element that does not sufficiently hinder movement of an outer member of an intraluminal device upon actuation of control handle 40. In one exemplary embodiment, base 58 may comprise a smooth curved surface, such as made from metal. In a preferred embodiment, base 58 may comprise a second roller. For illustrative purposes, base 58 will be referred to hereinafter as second roller 58.

First roller 56, and, in the preferred embodiment, second roller 58, may be made of any suitable material having a hardness in the range of about 65 to 80 Durometer Shore A. Examples of materials having a hardness falling within this range include, but are not limited to, polyurethane and silicone. In a preferred embodiment of the invention, first roller 56 and second roller 58 further comprise silica, which may be added in any suitable amount to improve traction of rollers 56 and 58.

In another exemplary embodiment of the invention, roller assembly 54 may further comprise a roller block 60, at least one roller pillow block, preferably a first roller pillow block 62 and a second roller pillow block 64, and at least one roller block spring, preferably a first roller block spring 82 and a second roller block spring 84. In a preferred embodiment first and second roller block springs 82 and 84 are compression springs. Roller block 60 is configured to move relative to first and second roller pillow blocks 62 and 64, which remain stationary relative to housing 42.

Control handle 40 further comprises a clamp assembly 66 positioned proximate to second end 48 of housing 42. Clamp assembly 66 comprises a first clamp element 68 and a second clamp element 70, which are aligned substantially symmetric about an axis parallel to longitudinal axis 44. As illustrated in FIG. 3, first clamp element 68 may comprise a press block and second clamp element 70 may comprise a portion of housing 42, although it will be appreciated that second clamp element 70 may comprise a unit or device separate from housing 42. In another exemplary embodiment of the invention, clamp assembly 66 may further comprise at least one clamp pillow block, preferably a first clamp pillow block 72 and a second clamp pillow block 74, and at least one clamp block spring, preferably a first clamp block spring 86 and a second clamp block spring 88. In a preferred embodiment, first and second clamp block springs 86 and 88 are compression springs. First clamp element 68 is configured to move relative to first and second clamp pillow blocks 72 and 74, which remain stationary relative to housing 42.

Control handle 40 also comprises a closure mechanism 100 connected to roller assembly 54 and clamp assembly 66. In one exemplary embodiment of the invention, closure mechanism 100 comprises a camshaft 78 and a cam lever 76. Camshaft 78 extends parallel to longitudinal axis 44 and is connected to cam lever 76 at approximately the center of camshaft 78, although it will be appreciated that cam lever 76 may be connected to camshaft 78 at any suitable point along camshaft 78. Camshaft 78 extends through roller assembly 54 and clamp assembly 66, as follows. In clamp assembly 66, camshaft 78 extends through first clamp pillow block 72, first clamp element 68 and second clamp pillow block 74. In roller assembly 54, camshaft 78 extends through first roller pillow block 62, roller block 60 and second roller pillow block 64. The sections of camshaft 78 that extend through roller block 60 and first clamp element 68 comprise a cam lobe 108a and 108b, respectively, formed by an offset portion. For example, lobes 108a and 108b may be formed as a flat or convex undercut portion in the otherwise cylindrical camshaft 78. The operation of roller assembly 54 and clamp assembly 66 by camshaft 78 will be described in detail below.

Control handle 40 also comprises a turn device 80, such as a thumb wheel as illustrated in FIGS. 3 and 4, a turn wheel, a turn lever, or the like. Turn device 80 is operably connected to roller assembly 54 and is configured to actuate roller assembly 54 when turn device 80 is rotated. In one exemplary embodiment illustrated in FIGS. 3-7, turn device 80 is operably connected to first roller 56 so that when turn device 80 is rotated, first roller 56 is rotated. Alternatively, turn device 80 may be connected similarly to second roller 58.

Figure 6:
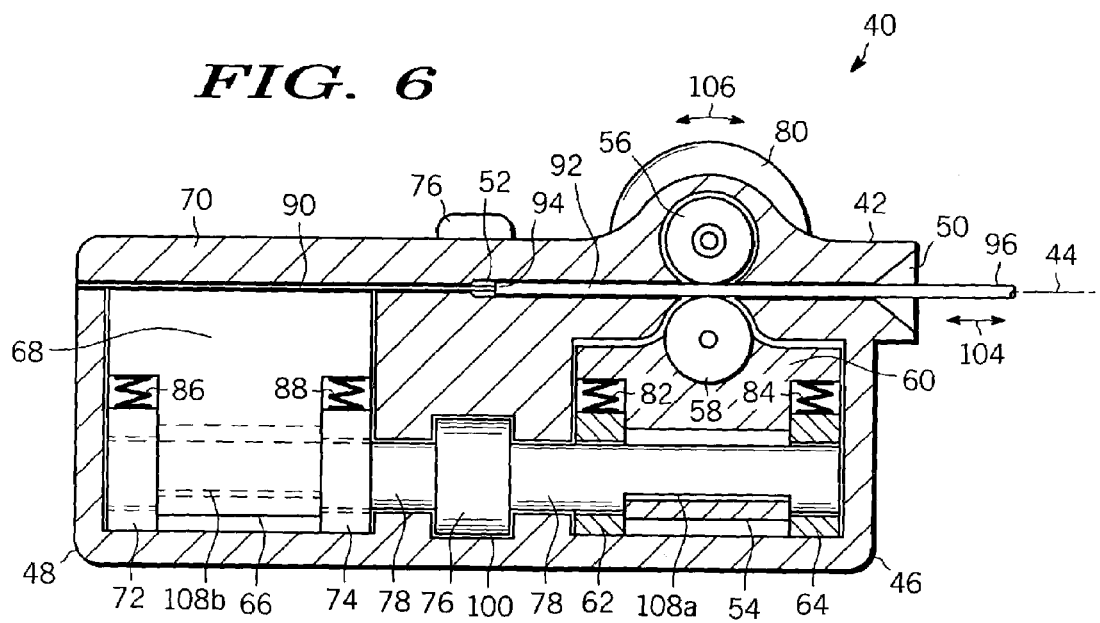
FIG. 6 is a cross-sectional view of the control handle of FIG. 3 with a portion of an intraluminal device inserted therein, the control handle in a closed position.

FIG. 6 illustrates control handle 40 in which an intraluminal device 96 comprising an inner member, such as a core wire 90 and an outer hollow tube or hypo tube 92 has been inserted. Core wire 90 is coaxially movably disposed within hypo tube 92 and extends beyond hypo tube 92 at a proximal end 94 of intraluminal device 96, which has been positioned within housing 42. To insert intraluminal device 96 into control handle 40, control handle 40 is opened by rotating cam lever 76 away from housing 42 (counterclockwise as viewed from end 48). Rotation of cam lever 76 counterclockwise in turn rotates camshaft 78 counterclockwise. Camshaft 78 is operatively connected to roller block 60 and first clamp element 68 by lobes 108a and 108b. Rotation of camshaft 78 counterclockwise causes lobe 108a to act against a through-bore in roller block 60 such that roller block 60 slides between first and second roller pillow blocks 62 and 64, and compresses first and second roller block springs 82 and 84. In this way, rotation of cam lever 76 counterclockwise moves roller block 60 and hence second roller 58 a sufficient distance from first roller 56 so that hypo tube 92 may be interposed between first roller 56 and second roller 58. In a similar fashion, rotation of camshaft 78 also causes lobe 108b to act against a through-bore in first clamp 68 such that first clamp 68 slides between first clamp pillow block 72 and second clamp pillow block 74, and compresses first and second clamp block springs 86 and 88. Again, rotation of cam lever 76 counterclockwise causes first clamp 68 to move a sufficient distance from second clamp element 70 so that core wire 90 may be interposed between first and second clamp elements 68 and 70.

With control handle 40 now in its open position, the transverse dimension of lumen 52 from first end 46 of housing 42 to second end 48 is sufficiently wide to receive core wire 90 and hypo tube 92, although it will be appreciated that the transverse dimension of lumen 52 may vary from first end 46 to second end 48. End 94 of intraluminal device 96 now may be inserted into entry port 50, that is, core wire 90 first may be inserted into entry port 50, followed by hypo tube 92. Intraluminal device 96 preferably is positioned within control handle 40 until core wire 90 abuts housing 42 at end 48.

Figure 7:
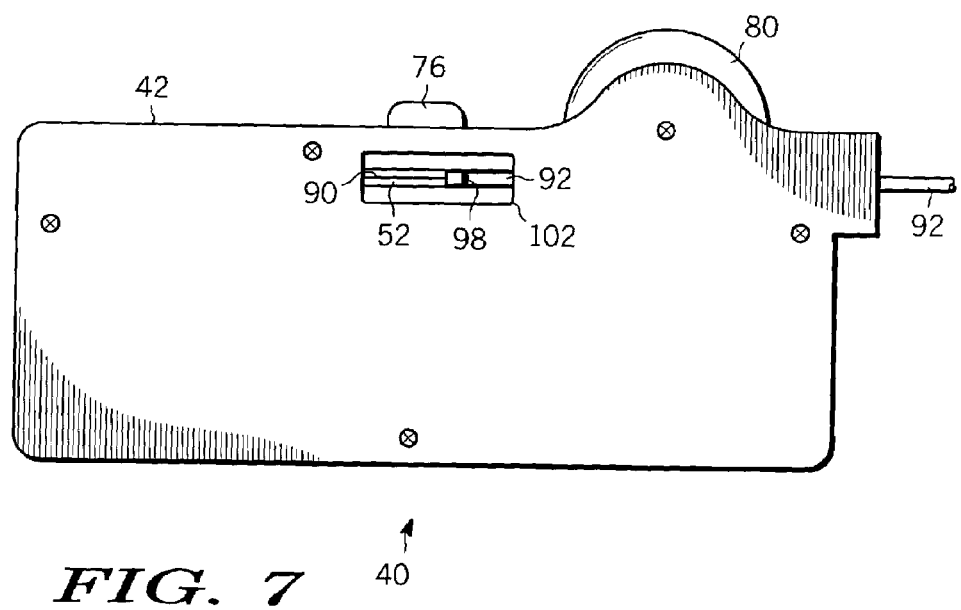
FIG. 7 is a back view of the control handle of FIG. 3 with a portion of an intraluminal device inserted therein, the control handle in a closed position.

Referring momentarily to FIG. 7, in another exemplary embodiment of the present invention, control handle 40 may further comprise a window 102 which is positioned within housing 42 approximately between roller assembly 54 and clamp assembly 66. Window 102 is configured to expose a portion of lumen 52 such that a marker 98, which is typically located toward the proximal end of hypo tube 92, may be viewed through window 102. Thus, intraluminal device 96 may be positioned within control handle 40 until marker 98 is viewable through window 102 and is positioned at a desired location within window 102, indicating that intraluminal device 96 is suitably positioned within housing 42.

Referring again to FIG. 6, once intraluminal device 96 has been suitably positioned within housing 42, with core wire 90 interposed between first clamp element 68 and second element 70 and hypo tube 92 interposed between first roller 56 and second roller 58, control handle 40 may be closed. To close control handle 40, cam lever 76 may be released from its open position. When cam lever 76 is released, cam lobe 108a is rotated out of engagement with the through-bore in roller block 60, thus permitting first and second roller block springs 82 and 84 to expand such that roller block 60 slides between first and second roller pillow blocks 62 and 64. Roller block 60 thus advances second roller 58 toward first roller 56 to decrease the transverse dimension of lumen 52 between first roller 56 and second roller 58 so that first roller 56 may make sufficient contact with hypo tube 92. As used herein, "sufficient contact" means that a suitable surface area of first roller 56 contacts hypo tube 92 at a suitable pressure applied by first and second roller block springs 82 and 84 so that, upon rotation of first roller 56, movement of hypo tube 92 along an axis parallel to axis 44 is effected. It will be appreciated that, while it is important that hypo tube 92 be held firmly between first roller 56 and second roller 58 so that sufficient contact may be made between first roller 56 and hypo tube 92, hypo tube 92 should not be held so tightly that it is crimped or otherwise damaged by rollers 56 and 58. Release of camshaft 78 also causes cam lobe 108b to be rotated out of engagement with the through-bore in first clamp element 68, thus permitting first and second clamp block springs 86 and 88 to expand such that first clamp 68 slides between first clamp pillow block 72 and second clamp pillow block 74. Thus, first clamp element 68 is caused to advance toward second clamp element 70 to decrease the transverse dimension of lumen 52 between first clamp element 68 and second clamp element 70 so that core wire 90 may be secured between first and second clamp elements 68 and 70 by the forces applied by first and second clamp block springs 86 and 88. When intraluminal device 96 has been suitably positioned within control handle 40, cam lever 76 may be placed in a locked position by rotating it toward housing 42 (clockwise as viewed from end 48).

Once intraluminal device 96 has been secured within control handle 40, hypo tube 92 may be moved relative to core wire 90 upon rotation of turn device 80. Manual rotation of turn device 80 results in rotation of first roller 56. Due to the friction between first roller 56 and hypo tube 92, first roller 56 causes hypo tube 92 to move into or out of control handle 40, as illustrated by arrows 104, depending on the direction turn device 80 is rotated, as illustrated by arrows 106. Because core wire 90 is held firmly between first and second clamp elements 66 and 70, core wire 90 remains stationary within housing 42 and hypo tube 92 moves relative to core wire 90. Accordingly, a clinician rotating turn device 80 is able to deploy or collapse an apparatus (not shown) at the distal end of intraluminal device 96.

After intraluminal device 96 has been operated, control handle 40 may be removed from intraluminal device 96 so that the device may be removed from the patient or so that another device may be passed over intraluminal device 96.

It will be appreciated that, while FIGS. 3-7 illustrate one embodiment of the present invention, various configurations of this embodiment are possible. For example, while roller assembly 54 is illustrated with roller block 60, first and second roller pillow blocks 62 and 64, and first and second roller block springs 82 and 84, it will be appreciated that roller assembly 54 may comprise any suitable mechanism that permits a hypo tube to be interposed between rollers 56 and 58 and that permits rollers 56 and 58 to make sufficient contact with the hypo tube so that, upon rotation of first roller 56, coaxial movement of the hypo tube relative to the core wire is effected. Similarly, while clamp assembly 66 is illustrated with first clamp element 68, second clamp element 70, first and second clamp pillow blocks 72 and, 74, and first and second clamp block springs 86 and 88, it will be appreciated that clamp assembly 66 may comprise any suitable mechanism that permits a core wire to be secured within control handle 40 so as to prevent longitudinal movement of the core wire relative to control handle 40. In addition, closure mechanism 100 may be configured so that handle 40, which can be configured normally in an open position, can be closed upon rotation of cam lever 76 or, alternatively, as illustrated above, closure mechanism 100 may be configured so that handle 40, normally configured in a closed position, can be opened upon rotation of cam lever 76.

Further, while control handle 40 is illustrated in FIGS. 3-7 with roller assembly 54 positioned proximate to end 46 for receiving a hypo tube between rollers 56 and 58 and with clamp assembly 66 positioned proximate to end 48 for receiving a core wire between clamp elements 68 and camshaft 78, it will be appreciated that, in another exemplary embodiment of the invention, control handle 40 may be configured so that roller assembly 54 is positioned proximate to end 48 to receive a core wire between rollers 56 and 58 and clamp assembly 66 is positioned proximate to end 46 to receive a hypo tube between clamp elements 68 and 70. In this embodiment, clamp assembly 66 should be configured so that, upon closing of the control handle, clamp elements 66 and 70 do not crimp or damage the hypo tube but hold it securely to prevent longitudinal movement relative to the control handle. Thus, upon rotation of turn wheel 80, first roller 56 may effect movement of the core wire relative to the hypo tube.

Moreover, while control handle 40 is illustrated in FIGS. 6 and 7 for use with an intraluminal device comprising a core wire and a hypo tube, it will be appreciated that the control handle of the present invention may be used for any suitable intraluminal device comprising an inner member, such as a core wire, a guidewire, an inner catheter, etc., a portion of which is coaxially movably disposed within an outer hollow member, such as a sheath, a shaft, a hypo tube, etc., and which utilizes a push and/or pull mechanism for deployment and/or collapsing of an apparatus associated with the device.

Figure 8:
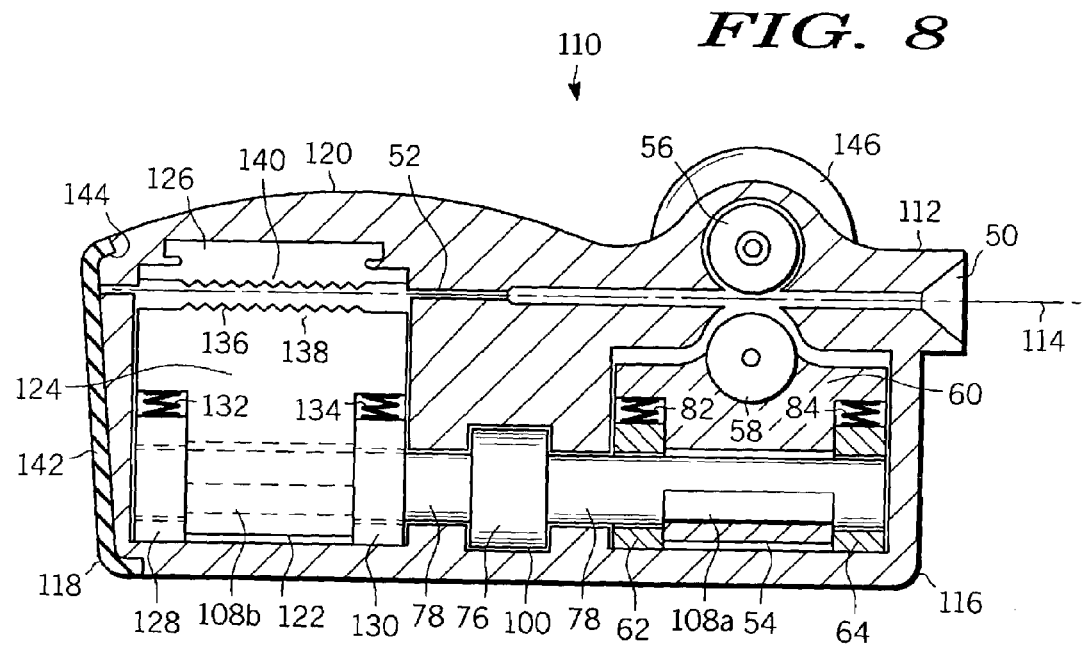
FIG. 8 is a cross-sectional view of a control handle for an intraluminal device in accordance with another exemplary embodiment of the invention, the control handle being in an open position.

FIG. 8 is a cross-sectional view of a control handle 110 in accordance with another exemplary embodiment of the present invention. Elements of FIG. 8 that have the same reference numbers as FIG. 3 are the same as the corresponding FIG. 3 elements. Control handle 110 comprises a housing 112 having a longitudinal axis 114, a first end 116 and a second end 118. Housing 112 further comprises a curved elevated top surface 120, which permits control handle 110 to be comfortably held by a clinician. At first end 116 of housing 112, control handle 110 comprises an entry port 50 configured to receive an inner member, such as a core wire, and an outer member, such as a hypo tube, of an intraluminal device. Entry port 50 is connected to a lumen 52 that is parallel to longitudinal axis 114 and extends from entry port 50 to second end 118 of housing 112. Housing 112 may be manufactured from any of the materials described above for the manufacture of housing 42 with reference to FIG. 3.

Control handle 110 further comprises roller assembly 54 positioned proximate to first end 116 of housing 112. Roller assembly 54 comprises first roller 56, second roller 58, roller block 60, first roller pillow block 62 and first roller block spring 82, and second roller pillow block 64 and second roller block spring 84.

Control handle 110 further comprises a clamp assembly 122 positioned proximate to second end 118 of housing 112. Clamp assembly 122 comprises a first clamp element 124, a second clamp element 126, a first clamp pillow block 128, a first clamp block spring 132, a second clamp pillow block 130, and a second clamp block spring 134. In another embodiment of the invention, first clamp element 124 and second clamp element 126 may have serrated teeth 136 or other suitable gripping mechanism on opposing surfaces 138 and 140, respectively, so as to grip a core wire securely. In a preferred embodiment, first and second clamp block springs 132 and 134 are compression springs. First clamp element 124 is configured to move relative to first and second clamp pillow blocks 128 and 130, which remain stationary relative to housing 112.

Control handle 110 also comprises closure mechanism 100. Camshaft 78 of closure mechanism 100 extends parallel to longitudinal axis 114 and is connected to cam lever 76 at approximately the center of camshaft 78, although it will be appreciated that cam lever 76 may be connected to camshaft 78 at any suitable point along camshaft 78. Camshaft 78 extends through roller assembly 54 and clamp assembly 122, as follows. In clamp assembly 122, camshaft 78 extends through first clamp pillow block 128, first clamp element 124 and second clamp pillow block 130. In roller assembly 54, camshaft 78 extends through first roller pillow block 62, roller block 60 and second roller pillow block 64. The sections of camshaft 78 that extend through roller block 60 and first clamp element 124 comprise cam lobe 108a and 108b, respectively, formed by an offset portion. For example, lobes 108a and 108b may be formed as a flat or convex undercut portion in the otherwise cylindrical camshaft 78. The operation of roller assembly 54 and clamp assembly 122 by camshaft 78 will be described in detail below. Control handle 112 also comprises turn wheel 146, which is operatively connected to first roller 56.

In another exemplary embodiment of the invention, control handle 112 further comprises a removable end cap 142 which may be positioned snugly over a lip 144 of housing 112 at second end 118. End cap 142 may serve as a stop for a core wire during insertion of an intraluminal device into control handle 110 or, alternatively, end cap 142 may be removed from housing 112 so that a core wire may be extended through lumen 52 and beyond control handle 110. This latter configuration may be useful for "over-the-wire (OTW)" procedures and guidewire extension procedures. End cap 142 may be formed of any suitable pliable elastomer material that permits end cap 142 to be easily removed from and replaced onto lip 144.

Figure 9:
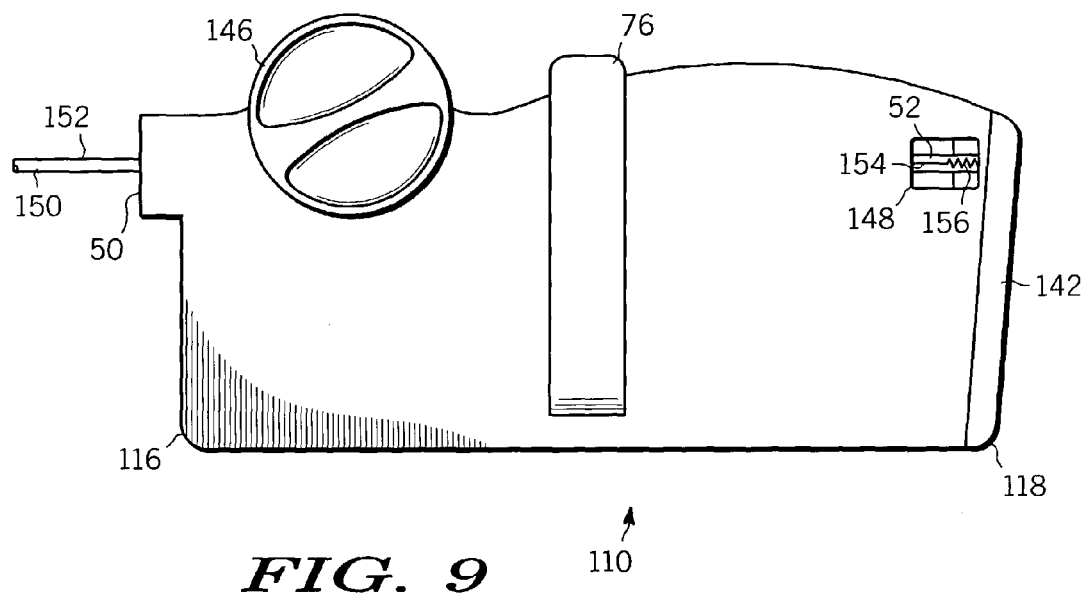
FIG. 9 is a front view of the control handle of FIG. 8 with a portion of an intraluminal device inserted therein, the control handle being in a closed position.

FIG. 9 is a back view of control handle 110 in a closed position with an intraluminal device 150 inserted therein. Intraluminal device 150 has a hypo tube 152 and a guidewire 154 disposed therein. In another exemplary embodiment of the invention, control handle 110 may comprise a magnifying window 148, which is positioned proximate to second end 118 of housing 112. Magnifying window 148 is configured to expose a portion of lumen 52 so that a clinician may better see a guidewire extension coupling 156 disposed at the end of the guidewire 154. Thus, by removing end cap 142 and viewing guidewire extension coupling 156 of guidewire 154 through magnifying window 148, a clinician may easily attach an end of a guidewire extension to guidewire extension coupling 156. Typically, the end of the guidewire extension and guidewire extension coupling 156 of the first guidewire 154 will have some type of suitable complementary male/female coupling arrangement to provide an end-to-end in-line coupling of the two guidewires.

Figure 10:
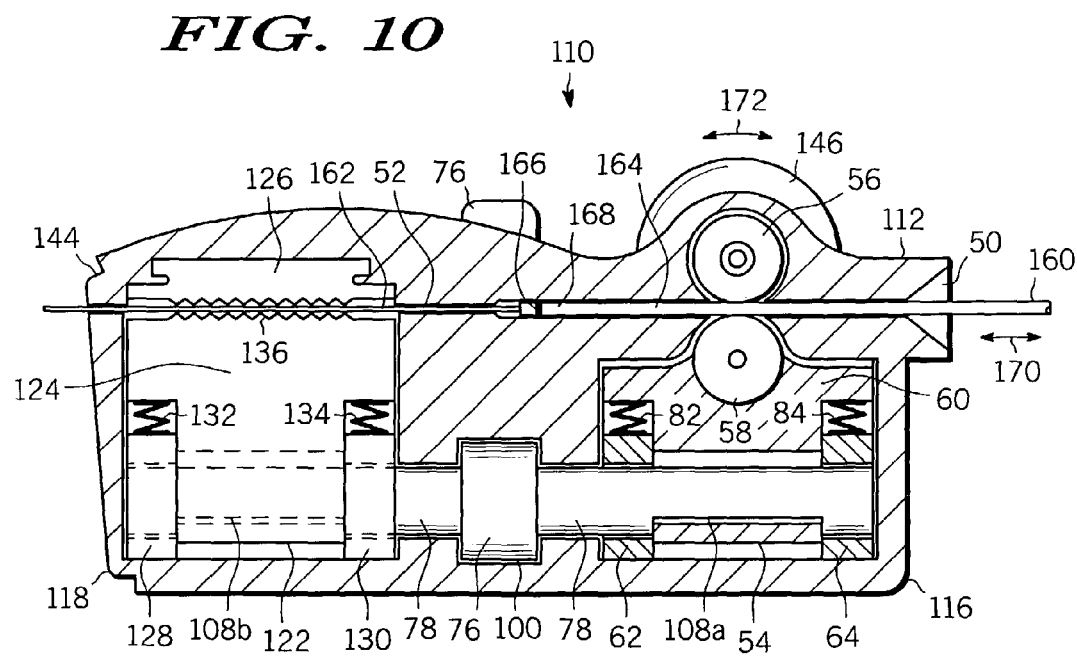
FIG. 10 is a cross-sectional view of the control handle of FIG. 8 with a portion of an intraluminal device inserted therein, the control handle being in a closed position.

FIG. 10 illustrates control handle 110 in which an intraluminal device 160 comprising a core wire 162 and an outer hollow tube or hypo tube 164 has been inserted. Hypo tube 164 further comprises a marker 166. Core wire 162 is disposed within hypo tube 164 and extends beyond hypo tube 164 at an end 168 of intraluminal device 160, which has been positioned within housing 112. To insert intraluminal device 160 into control handle 110, control handle 110 is opened by rotating cam lever 76 away from housing 112 (counterclockwise as viewed from second end 118). Rotation of cam lever 76 away from housing 112 in turn rotates camshaft 78 counterclockwise. Camshaft 78 is operatively connected to roller block 60 and first clamp element 124 by lobes 108a and 108b. Rotation of camshaft 78 counterclockwise causes lobe 108a to act against a through-bore in roller block 60 such that roller block 60 slides between first and second roller pillow blocks 62 and 64 and compresses first and second roller block springs 82 and 84. In this way, rotation of cam lever 76 counterclockwise moves roller block 60, and hence second roller 58, a sufficient distance from first roller 56 so that hypo tube 164 may be interposed between first roller 56 and second roller 58. In a similar fashion, rotation of camshaft 78 also causes lobe 108b to act against a through-bore in first clamp element 124 such that first clamp element 124 slides between first clamp pillow block 128 and second clamp pillow block 130, and compresses first and second clamp block springs 132 and 134. Again, rotation of cam lever 76 counterclockwise causes first clamp element 124 to move a sufficient distance from second clamp element 126 so that core wire 162 may be interposed between first and second clamp elements 124 and 126.

With control handle 110 now in its open position, the transverse dimension of lumen 52 from first end 116 of housing 112 to second end 118 is sufficiently wide to receive core wire 162 and hypo tube 164, although it will be appreciated that the transverse dimension of lumen 52 may vary from first end 116 to second end 118. End 168 of intraluminal device 160 now may be inserted into entry port 50, that is, core wire 162 first may be inserted into entry port 50, followed by hypo tube 164. While intraluminal device 160 may be positioned within control handle 110 until core wire 162 abuts end cap 142 (not shown), in another exemplary embodiment of the invention, as illustrated in FIG. 10, end cap 142 may be removed from control handle 112 and intraluminal device 160 may be positioned within control handle 110 until core wire 162 passes through control handle 110. This configuration may be used in various procedures such as, for example, "over the wire (OTW)" procedures during which a clinician intends to pass another device over core wire 162. Accordingly, to suitably position intraluminal device 160 within control handle 110, a clinician may align marker 166 on hypo tube 164 so that it is appropriately viewable in a window in housing 112 (not shown), such as window 102 of housing 42 illustrated in FIG. 7.

Referring again to FIG. 10, once intraluminal device 160 has been positioned appropriately within housing 112, with core wire 162 interposed between first clamp element 124 and second element 126 and hypo tube 164 interposed between first roller 56 and second roller 58, control handle 110 may be closed. To close control handle 110, cam lever 76 may be released from its open position. When cam lever 76 is released, cam lobe 108a is rotated out of engagement with the through-bore in roller block 60, thus permitting first and second roller block springs 82 and 84 to expand such that roller block 60 slides between first and second roller pillow block 62 and 64. Roller block 60 thus advances second roller 58 toward first roller 56 to decrease the transverse dimension of lumen 52 between first roller 56 and second roller 58 so that first roller 56 may make sufficient contact with hypo tube 164. It will be appreciated that, while it is important that hypo tube 164 be held firmly between first roller 56 and second roller 58, hypo tube 164 should not be held so tightly that it is crimped or otherwise damaged by rollers 56 and 58. Release of camshaft 78 also causes cam lobe 108b to be rotated out of engagement with the through-bore in first clamp element 124, thus permitting first and second clamp block springs 132 and 134 to expand such that first clamp element 124 slides between first clamp pillow block 128 and second clamp pillow block 130. Thus, first clamp element 124 is caused to advance toward second clamp element 126 to decrease the transverse dimension of lumen 52 between first clamp element 124 and second clamp element 126 so that core wire 162 may be secured between first and second clamp elements 124 and 126 by the forces applied by first and second clamp block springs 132 and 134.

Serrated teeth 136 of first and second clamp elements 124 and 126 then grip core wire 162 so as to prevent longitudinal movement of core wire 162 relative to control handle 110. When intraluminal device 160 has been suitably positioned within control handle 110, cam lever 76 may be placed in a locked position by rotating it toward housing 112 (clockwise as viewed by second end 118).

Once intraluminal device 160 has been secured within control handle 110, hypo tube 164 may be moved relative to core wire 162 upon rotation of turn wheel 146. Manual rotation of turn wheel 146 results in rotation of first roller 56. Due to the friction between first roller 56 and hypo tube 150, first roller 56 causes hypo tube to move into or out of control handle 110, as illustrated by arrows 170, depending on the direction turn wheel 146 is rotated, as illustrated by arrows 172. Because core wire 162 is held firmly between first and second clamp elements 124 and 126, core wire 162 remains stationary within housing 112 and hypo tube 164 moves coaxially relative to core wire 162. Accordingly, a clinician rotating turn wheel 146 is able to deploy or collapse an apparatus (not shown) at the distal end of intraluminal device 160.

After intraluminal device 160 has been operated, control handle 110 may be removed from intraluminal device 160 so that the device may be removed from the patient or so that another device may be passed over intraluminal device 160.

Thus, there has been provided, in accordance with the invention, a control handle for an intraluminal device that fully meets the needs set forth above. The control handle is configured to accurately deploy an intraluminal device that utilizes a push and/or pull mechanism for deployment. Although various embodiments of the invention have been described and illustrated with reference to particular embodiments thereof, it is not intended that the invention be limited to such illustrative embodiments. For example, closure mechanism 100 may comprise any suitable mechanism configured to change the transverse dimension of the lumen between the first and second clamp elements and the first roller and the base. Further, the closure mechanism need not be located between the clamp assembly and the roller assembly. Additionally, the handle housing may have any suitable shape, including any suitable ergonomic shape. Those of skill in the art will recognize that many variations and modifications of such embodiments are possible without departing from the spirit of the invention. Accordingly, it is intended to encompass within the invention all such modifications and variations as fall within the scope of the appended claims.

Benefits, other advantages, and solutions to problems have been described above with regard to specific embodiments. However, the benefits, advantages, solutions to problems, and any element(s) that may cause any benefit, advantage, or solution to occur or become more pronounced are not to be construed as a critical, required, or essential features or elements of any or all the claims. As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A control handle for an intraluminal device, the control handle comprising:

a handle housing comprising a lumen, said handle housing having a first end and a second end;

a roller assembly disposed at a first end of said lumen, said roller assembly comprising a first roller and a base, said lumen interposed between said first roller and said base;

a clamp assembly disposed at a second end of said lumen, said clamp assembly comprising a first clamp element and a second clamp element, said lumen interposed between said first clamp element and said second clamp element;

a closure mechanism configured to effect movement between said first clamp element and said second clamp element and between said first roller and said base; and a turn device operably connected to said roller assembly.

2. The control handle of claim 1, said handle housing further comprising an entry port at said first end of said handle housing and connected to said first end of said lumen.

3. The control handle of claim 1, further comprising a window disposed within said handle housing and configured to expose a portion of said lumen.

4. The control handle of claim 1, further comprising a magnifying window disposed within said handle housing and configured to permit viewing of a portion of said lumen.

5. The control handle of claim 1, wherein said lumen is open at said first end and closed at said second end.

6. The control handle of claim 1, wherein said lumen is open at said first end and said second end.

7. The control handle of claim 6, further comprising a removable end cap configured for placement over an end of said handle housing proximate said second end of said lumen.

8. The control handle of claim 1, said first roller having a hardness in the range of about 65 to 80 Durometer Shore A.

9. The control handle of claim 1, said first roller comprising silica.

10. The control handle of claim 1, said base comprising a second roller.

11. The control handle of claim 10, said second roller having a hardness in the range of about 65 to 80 Durometer Shore A.

12. The control handle of claim 11, said second roller comprising silica.

13. The control handle of claim 1, said first clamp element and said second clamp element comprising a gripping mechanism on opposing surfaces.

14. The control handle of claim 1, said turn device comprising one selected from the group comprising a turn wheel, a thumb wheel and a turn lever.

15. The control handle of claim 1, said closure mechanism comprising a camshaft operably connected to a cam lever, said camshaft operably connected to said clamp assembly and said roller assembly.

16. The control handle of claim 1, said roller assembly comprising a roller block, at least one roller block and at least one roller block spring.

17. The control handle of claim 1, said clamp assembly comprising at least one clamp pillow block and at least one clamp block spring.

18. The control handle of claim 1, said turn device operably connected to said first roller.

19. The control handle of claim 1, said base comprising a second roller.

20. The control handle of claim 19, said second roller having a hardness in the range of about 65 to 80 Durometer Shore A.

21. The control handle of claim 20, said second roller comprising silica.

22. A control handle for effecting movement between an outer hollow tube relative to an inner member coaxially movably disposed within the outer hollow tube and extending beyond the outer hollow tube at a first end of the outer hollow tube, the control handle comprising;

a handle housing having an first axis, a first end and a second end;

a roller assembly disposed at least partially within said handle housing, said roller assembly comprising a first roller and a base, said first roller and said base aligned substantially symmetric about an axis parallel to said first axis and disposed a sufficient distance from each other so that the outer hollow tube may be interposed between said first roller and said base;

a clamp mechanism disposed within said handle housing, said clamp mechanism comprising a first clamp element and a second clamp element, said first and second clamp elements aligned substantially symmetric about an axis parallel said first axis and disposed a sufficient distance from each other so that the inner member may be interposed between said first and second clamp elements;

a closure mechanism configured to effect movement between said first clamp element and said second clamp element so that the inner member may be secured between said first and second clamp element to prevent movement of the inner member relative to the control handle along said first axis and to effect movement between said first roller and said base so that said first roller may make sufficient contact with the outer hollow tube; and a turn device operably connected to said roller assembly and configured to effect rotational movement of said first roller upon rotation of aid turn device.

23. The control handle of claim 22, said handle housing further comprising an entry port at said first end of said handle housing, said entry port configured to receive the inner member and outer hollow tube.

24. The control handle of claim 22, further comprising a window disposed within said handle housing, said window configured to permit viewing of a portion of said outer hollow tube.

25. The control handle of claim 22, further comprising a magnifying window disposed within said handle housing and configured to permit viewing of a portion of said inner member.

26. The control handle of claim 22, said handle housing closed at said second end of said handle housing.

27. The control handle of claim 22, said handle housing open at said second end of said handle housing so that said inner member may extend through said handle housing and beyond said handle housing.

28. The control handle of claim 24, further comprising a removable end cap configured for placement over said second end of said handle housing.

29. The control handle of claim 22, said first roller having a hardness in the range of about 65 to 80 Durometer Shore A.

30. The control handle of claim 29, said first roller comprising silica.

31. The control handle of claim 22, said base comprising a second roller.

32. The control handle of claim 31, said second roller having a hardness in the range of about 65 to 80 Durometer Shore A.

33. The control handle of claim 32, said second roller comprising silica.

34. The control handle of claim 22, said first clamp element and said second clamp element comprising a gripping mechanism on opposing surfaces.

35. The control handle of claim 22, said turn device comprising one selected from the group comprising a turn wheel, a thumb wheel and a turn lever.

36. The control handle of claim 22, said closure mechanism comprising a camshaft operably connected to a cam lever, said camshaft operably connected to said clamp assembly and said roller assembly.

37. The control handle of claim 22, said turn device operably connected to said first roller.

38. A control handle for an intraluminal device, the control handle comprising:
- a handle housing comprising a lumen, said handle housing having a first end and a second end;
- a roller assembly disposed at a first end of said lumen, said roller assembly comprising a first roller and a base, said lumen interposed between said first roller and said base;
- a clamp assembly disposed at a second end of said lumen, said clamp assembly comprsing a first clamp element and a second clamp element, said lumen interposed between said first clamp element and said second clamp element;
- a closure mechanism operably connected to said first roller assembly and said clamp assembly; and
- a turn device operably connected to said roller assembly.

39. The control handle of claim 38, further comprising a window disposed within said handle housing proximate to said roller assembly.

40. The control handle of claim 38, further comprising a magnifying window disposed within said handle housing proximate to said clamp assembly.

41. The control handle of claim 38, wherein said lumen is open at said first end and closed at said second end.

42. The control handle of claim 38, wherein said lumen is open at said first end and said second end.

43. The control handle of claim 42, further comprising a removable end cap configured for placement over an end of said handle housing proximate said second end of said lumen.

44. The control handle of claim 38, said first roller having a hardness in the range of about 65 to 80 Durometer Shore A.

45. The control handle of claim 38, said first roller comprising silica.

46. The control handle of claim 38, said first clamp element and said second clamp element comprising a gripping mechanism on opposing surfaces.

47. The control handle of claim 38, said turn device comprising one selected from the group comprising a turn wheel, a thumb wheel and a turn lever.

48. The control handle of claim 38, said closure mechanism comprising a camshaft operably connected to a cam lever, said camshaft operably connected to said clamp assembly and said roller assembly.

49. The control handle of claim 38, said turn device operably connected to said first roller.

* * * * *